US008617587B2

(12) United States Patent
Thoma et al.

(10) Patent No.: US 8,617,587 B2
(45) Date of Patent: Dec. 31, 2013

(54) TASTED MASKED VETERINARY SOLID COMPOSITIONS

(75) Inventors: Hubert Thoma, Pfaffenweiler (DE); Uwe Thomas Schote, Basel (CH); Ute Isele, Freiburg (DE)

(73) Assignee: Novartis AG, Basel (CH)

( * ) Notice: Subject to any disclaimer, the term of this patent is extended or adjusted under 35 U.S.C. 154(b) by 879 days.

(21) Appl. No.: 12/630,422

(22) Filed: Dec. 3, 2009

(65) Prior Publication Data
US 2010/0074952 A1 Mar. 25, 2010

Related U.S. Application Data

(63) Continuation of application No. 10/506,937, filed as application No. PCT/EP03/02446 on Mar. 10, 2003, now abandoned.

(30) Foreign Application Priority Data

Mar. 11, 2002 (EP) .................................... 02005511

(51) Int. Cl.
*A61K 9/20* (2006.01)
(52) U.S. Cl.
USPC ...... 424/442; 424/195.16; 424/464; 424/465; 424/468; 424/469; 424/474; 426/2; 426/805; 514/212.07
(58) Field of Classification Search
None
See application file for complete search history.

(56) References Cited

U.S. PATENT DOCUMENTS

| | | | |
|---|---|---|---|
| 3,231,466 A | 1/1966 | Scott et al. ..................... 514/576 |
| 3,824,233 A | 7/1974 | Friedman ......................... 549/74 |
| 3,937,825 A | 2/1976 | Alford ........................... 514/129 |
| 4,708,867 A | 11/1987 | Hsiao | |
| 4,892,740 A | 1/1990 | Takasima et al. | |
| 6,149,943 A | 11/2000 | McTeigue et al. ............ 424/494 |
| 2003/0190343 A1 | 10/2003 | Thombre et al. | |

FOREIGN PATENT DOCUMENTS

| | | |
|---|---|---|
| WO | 8803795 | 6/1988 |
| WO | 9115194 | 10/1991 |
| WO | 9324109 | 12/1993 |
| WO | WO 96/01621 | 6/1995 |
| WO | WO 95/31963 | 11/1995 |
| WO | WO 97/25066 | 7/1997 |
| WO | 9816111 | 4/1998 |
| WO | 0045794 | 8/2000 |
| WO | WO 01/35925 | 5/2001 |
| WO | WO 01/37808 | 5/2001 |
| WO | WO 01/49272 | 7/2001 |
| WO | 0174390 | 10/2001 |
| WO | WO 02/071874 | 9/2006 |

OTHER PUBLICATIONS

Jones—Veterinary Pharmacology & Therapeutics, pp. 832-834, 843—(1957).

*Primary Examiner* — Neil Levy
(74) *Attorney, Agent, or Firm* — Ann R. Pokalsky, Esq.; Dilworth & Barrese, LLP

(57) ABSTRACT

The present invention relates to the supply and production of an animal medicine consisting of a substrate in pellet or tablet form, which is attractive to livestock and domestic animals, in which fine-grained particles of a neutral-tasting, physiologically compatible, solid carrier material are embedded, which is characterized in that said fine-grained particles of carrier material have an average diameter of 0.09 to 0.8 mm and are coated with an active substance from veterinary medicine, and said active substance layer is covered with a protective layer of a physiologically compatible polymer matrix, and to the production of this animal medicine. It also relates to the usage of said double-coated, fine-grained particles of carrier material in the production of a preparation for veterinary medicine.

7 Claims, No Drawings

TASTED MASKED VETERINARY SOLID COMPOSITIONS

RELATED APPLICATIONS

This application is a continuation of U.S. Ser. No. 10/506,937, filed Oct. 13, 2004, now abandoned which is a National Phase Application under §371 of International Application No. PCT/EP03/02446 filed Mar. 10, 2003, each of which are hereby incorporated in their entirety.

The present invention relates to the preparation of an animal medicine in an application form, which contains the active ingredient in a stabilised form that masks the taste, and which is readily taken orally by an animal. The present invention is concerned in particular with those embodiments that contain bitter, bad-tasting active ingredients or those which are unpleasant for the animal in another respect.

While, in humans, medicaments may be administered in a wide variety of application forms, such as tablets, coated tablets, emulsions, injection solutions, suppositories and the like, because the discipline and the desire to recover in human patients can be relied upon, in the case of animals practical problems are soon encountered, since a few application forms, such as the usage of suppositories, either have to be dispensed with all together or other forms, such as injections, must only be carried out by the veterinarian.

In general, humans do not like to visit the doctor. Since the animals concerned are domestic animals or productive livestock, the animal keeper prefers to use those treatment methods that he can carry out himself without a veterinarian. Among the preferred treatment methods, which an animal keeper can carry out himself, e.g. following the veterinarian's instructions, is the oral administration of medicaments.

Treating humans with medicines is generally not problematic, because the human patient follows the advice of the doctor or reads the directions on the leaflet in the pack and complies with them since this is in his own interest, and because the manufacturer usually prepares the tablet, capsule or coated tablet in a form which is appropriate for oral consumption and has been tailored for human patients.

As soon as a pharmaceutical active ingredient has a taste which is unpleasant to the animal, whether because it is bitter or has some other unpleasant taste or is simply alien to the animal, the animal refuses to take it orally. This inborn behaviour occurs to varying degrees among the different species of animals, and essentially depends on their conventional eating habits. Unfortunately, only a few active ingredients have a neutral taste, so that the problem being discussed here is almost always present.

In the case of a human patient, an unpleasant tasting active ingredient can be masked relatively easily, e.g. by coating it with a neutral-tasting or sweet layer. Everybody has come across gelatin capsules or tablets coated with sugar or lacquer at some time or other. It is easy to instruct the human patient to take the preparation without chewing.

An animal must have a natural willingness to take a medicinal preparation orally. Of course, an individual animal or a few animals can also be forced to take a medicament, by making it swallow or by injecting it. However, such forced methods are unacceptable to large animal operations, as they are labour-intensive, require the veterinarian in every individual case and ultimately lead to high costs, which in view of the current struggles for competition, cannot be passed onto meat or milk consumers. Therefore, when keeping animals on a large scale, simple and safe application forms are required, which, after diagnosis and indication by the veterinarian, can be given as independently as possible or even fully automatically, and which keep costs down to a tolerable amount.

One method which carries weight under these circumstances is the precisely dosed administration of animal medicines in the form of dry animal feed, so-called feed pellets or feed tablets into which the animal medicine has been incorporated. The term "feed" here is not restricted exclusively to substances which would normally be described as feed, but also to nutritional additives, e.g. yeast, starch, various types of sugar, etc.

Nowadays, domestic animals and productive livestock, e.g. pigs, also cattle, sheep and poultry, are often kept in animal housing which is equipped with the most modern, fully automatic feeding installations. In these, the fodder is apportioned fully automatically in accordance with the age and weight of the animal, and is transported to each animal at quite specific times of day and in daily amounts, and is either placed on its own in the trough or is mixed with the usual feed ration.

In such fully automated plants, the much-discussed feed pellets are used. The feed in question is compressed, highly compacted energy feed on a vegetable and/or animal basis, which may be enriched with additives such as proteins, vitamins and minerals. These feed pellets are no more than artificial, free-flowing, round or oblong grains, balls or even rod-shaped objects, depending on the manufacturing process, of a uniform size tailored to the species and age of the animals, which may have an average cross-section from a few millimetres for poultry to ca. one centimetre for adult pigs and cattle. Feed pellets are prepared by commercial fodder mills by grinding the organic starting material, mixing the components in the desired composition and finally compressing into pellets, then filled into sacks and delivered to the animal keeper, who fills and dispenses them into the distribution plant. An important advantage of these pellets is their simple handling which is a result of their uniformity, their fluidity and their stability in storage. They can be easily filled and dispensed, transported via conveyor belts or pipelines and administered to each animal in a precisely proportioned amount, all fully automatically. In addition, pellets take up significantly less space than fresh feed and, in particular, are eaten willingly and without problems by the animals, provided that they do not contain components which are found to be unpleasant or repulsive by the animal's sense of taste and smell.

There is therefore the possibility of adding to these pellets not only proteins and other vital substances such as vitamins and minerals, but also animal medicines when needed. In practice, this is already being carried out, but the depicted acceptance problems in the case of unpleasant tasting or unpleasant smelling active ingredients as discussed above are encountered.

In addition, there are stability problems when manufacturing feed pellets. In conventional production processes for feed pellets, dry organic starting material of animal or vegetable origin is ground, mixed thoroughly with the particles which are masked according to the invention and optionally with further additives, vitamins or trace elements, etc., i.e. substantially homogenised and then moistened with ca. 5 to 10 percent by weight water and compressed into pellets at elevated temperatures of ca. 80 to 100° C., preferably 60 to 90° C., under a pressure of ca. 1 to 100 kbar. The retention time in the press is ca. 5 to 180 seconds, preferably 10 to 90 seconds, and depends inter alia on the size of the pellets.

While many active ingredients which can be used in veterinary medicine withstand these temperatures quite well in pure form and can even be stored at room temperature for months and years without any measurable loss of activity, many of them decompose relatively quickly under pressure and when in intimate contact with animal or vegetable fodder fibres and at the prevailing temperature of 80 to 100° C. Contact with the fibres appears to catalyst the decomposition process. Even if the phase involving the raised pressure and elevated temperature are kept as short as is technically possible, and the finished pellets are immediately cooled to room temperature directly after the compression process, about one quarter to one third of the active ingredient is still lost. The decomposed products usually do not have any adverse effects on the treated animals, but the unavoidable loss of active ingredient must without doubt lead to a considerable increase in cost of the end product, since a substantially higher quantity has to be used.

This relative instability has also led to the fact that exact dosaging of the active ingredient in the form of feed pellets could only be previously ensured for ca. 4 to 6 weeks after production of the pellet. Therefore, the animal keepers were forced to use only relatively freshly produced pellets. They could not pursue meaningful long-term storage and had to place a new production request with the feed mills every four to six weeks, so that fresh fodder with a guaranteed content of antibiotics would be available to them. Though technically feasible, there is a high degree of logistics involved and means that the feed mills always have to produce small orders which do not necessarily suit their production programme, leading to unpleasant waiting times and especially to additional expense of the pellets.

In the present invention, the technical problems depicted in connection with feed pellets can be very easily resolved and pellets can be prepared, which are taken orally by the animals without problems.

When reviewing the administration of capsules and coated tablets to animals, it has been shown that these application forms are rather unsuitable for animal medicine, since in the case of herd animals they can only be used in a controlled manner with considerable effort on a daily basis, and in the case of pets, such as dogs and cats, lead to particular acceptance problems. The eating habits of animals generally play a decisive role when using oral application forms.

In the case of dogs, it has been observed that they gnaw at solid food, e.g. on bones, and gulp down other food, either in the form of large scraps or wet formulated food, almost unchewed. If a tablet or coated tablet is mixed with the wet formulated feed, very different results are obtained. In a few cases, the tablet is not noticed by the dog at all and is simply gulped down, and in other cases it remains uneaten in the dog bowl. In contrast to dogs, cats are considerably more fastidious in their eating habits. Only in the rarest cases can a tablet or coated tablet be mixed with the formulated food, without them noticing it immediately and rejecting it. Although cats also to not exactly chew their food, they generally break it down with a few small bites. They thereby damage the protective coating of a tablet or capsule and release the unpleasant tasting active ingredient. Attempts to mix the active ingredient directly with the feed likewise fail, because either the degree of dilution is insufficient to neutralise the unpleasant taste or the active ingredient breaks down too rapidly when in contact with the feed. For the same reasons, mixtures of feed, active ingredient and excipients, which stimulate the appetite of dogs and cats, similarly do not have a successful outcome with cats. Excipients which stimulate the appetite can be used per se for dogs and cats, for example natural and artificial cheese, meat and fish flavourings or flavour enhancers known from the foodstuff industry. However, whereas the test animals rush eagerly to a placebo which has a corresponding appetite stimulant, i.e. a tablet consisting of feed, flavouring and other excipients, but no active ingredient, the test animals reject the same combination as soon as active ingredient is added. Clearly, a different technical solution must be found to the existing problem with animals.

In the present invention, benazepril has been selected as the model active ingredient. As is known, benazepril has an extremely bitter taste and is not willingly taken orally by pigs, dogs and in particular cats. Benazepril is the chemical substance [S—(R*,R*)]-3-[[1-(ethoxycarbonyl)-3-phenylpropyl]amino]-2,3,4,5-tetrahydro-2-oxo-1H-1-benzazepin-1-acetic acid with the CAS registration number [86541-75-5].

Benazepril has the following chemical structure:

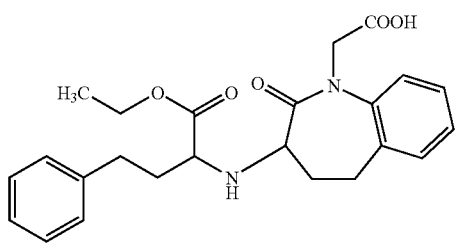 [SMILES: CCOC(=O)C(CCc1ccccc1)NC1CCc2ccccc2N(CC(=O)O)C1=O]

For medicinal purposes, this substance is usually used in the form of the hydrochloride, as it is in the present case. Benazepril is known from EP-0,072,352, and is used in animal medicine under the name FORTEKOR®, especially in the form of tablets, to treat cardiac and renal insufficiency.

It goes without saying that benazepril only represents a preferred embodiment of the present invention and is only intended to illustrate the invention by way of an application example. Of course, any other active ingredient which is suitable for animals can be administered according to the invention, but especially those active ingredients that have the taste disadvantages mentioned initially and are therefore not willingly taken orally by animals. Basically, a diversity of individual active ingredients or mixtures of active ingredients may be considered, e.g. those acting against external or internal parasites or active ingredients acting against viral or bacterial diseases, active ingredients acting against behavioural disorders, active ingredients acting against dysfunction, such as hypo- or hyper-activity, and the like. External parasites are understood in this case to be parasites which normally live on the animal, e.g. biting insects, such as mosquitos, fleas or lice, or members of the order Acarina, e.g. mites or ticks. The internal parasites include all species of worm infestation and bacterial diseases, in particular those infections that infest the organs or parts of the body designated as being preferred, such as the lungs, heart, alimentary tract or extremities, or which spread through the whole organism. Substances which can be used for these diseases are e.g. avermectins, milbemycins and derivatives thereof, such as ivermectin, selamectin, doramectin, moxidectin, nemadectin, abamectin, cydectin, milbemycinoxim, and also praziquantel, pyrantel, triclabendazol, and many more. Antimicrobial active ingredients are suitable, e.g. various penicillins, tetracyclines, sulfonamides, cephalosporins, cephamycins, aminoglucosids, trimethoprim, dimetridazoles, erythromycin, framycetin, fruazolidone, thiamulin, valnemulin, various macrolides, streptomycin and substances acting against protozoa, e.g. clopidol, salinomycin, monensin, halofuginone, narasin, robenidine, etc. Behavioural disorders include e.g. separation worry or travel sickness of dogs and cats. By dysfunction or hypo-activity are understood functions which deviate from the norm, whether through inborn or acquired damage to individual organs or tissue. This complex also includes rheumatic diseases, pathological changes to joints, bones or internal organs, and much more.

Biocides that may be used according to the invention, e.g. those named below, have been known to specialists for a long time. They include insecticides and acaricides with a varying mechanism of activity, e.g. chitin synthesis inhibitors, growth regulators; active ingredients which act as juvenile hormones; active ingredients which act as adulticides; and similarly, broad-band insecticides, broad-band acaricides. Nematicides may also be used according to the invention against helminthic infestations; and also the long-known anthelminthics and insect- and/or acarid-deterring substances.

Non-limitative examples of suitable insecticides and acaricides are:

1. Abamectin
2. AC 303 630
3. Acephat
4. Acrinathrin
5. Alanycarb
6. Aldicarb
7. alpha-Cypermethrin
8. Alphamethrin
9. Amitraz
10. Avermectin $B_1$
11. AZ 60541
12. Azinphos A
13. Azinphos M
14. Azinphos-methyl
15. Azocyclotin
16. *Bacillus subtil.* toxin
17. Bendiocarb
18. Benfuracarb
19. Bensultap
20. Cyfluthrin
21. Bifenthrin
22. BPMC
23. Brofenprox
24. Bromophos A
25. Bufencarb
26. Buprofezin
27. Butocarboxin
28. Butylpyridaben
29. Cadusafos
30. Carbaryl
31. Carbofuran
32. Carbophenthion
33. Cartap
34. Chloethocarb
35. Chlorethoxyfos
36. Chlorfenapyr
37. Chlorfluazuron
38. Chlormephos
39. Chlorpyrifos
40. Cis-Resmethrin
41. Clocythrin
42. Clofentezin
43. Cyanophos
44. Cycloprothrin
45. Cyfluthrin
46. Cyhexatin
47. D 2341
48. Deltamethrin
49. Demeton M
50. Demeton S
51. Demeton-S-methyl
52. Dibutylaminothio
53. Dichlofenthion
54. Dicliphos
55. Diethion
56. Diflubenzuron
57. Dimethoat
58. Dimethylvinphos
59. Dioxathion
60. DPX-MP062

-continued

61. Edifenphos
62. Emamectin
63. Endosulfan
64. Esfenvalerat
65. Ethiofencarb
66. Ethion
67. Ethofenprox
68. Ethoprophos
69. Etrimphos
70. Fenamiphos
71. Fenazaquin
72. Fenbutatinoxid
73. Fenitrothion
74. Fenobucarb
75. Fenothiocarb
76. Fenoxycarb
77. Fenpropathrin
78. Fenpyrad
79. Fenpyroximate
80. Fenthion
81. Fenvalerate
82. Fipronil
83. Fluazinam
84. Fluazuron
85. Flucycloxuron
86. Flucythrinat
87. Flufenoxuron
88. Flufenprox
89. Fonophos
90. Formothion
91. Fosthiazat
92. Fubfenprox
93. HCH
94. Heptenophos
95. Hexaflumuron
96. Hexythiazox
97. Hydroprene
98. Imidacloprid
99. insect-active fungi
100. insect-active nematodes
101. insect-active viruses
102. Iprobenfos
103. Isofenphos
104. Isoprocarb
105. Isoxathion
106. Ivermectin
107. Cyhalothrin
108. Lufenuron
109. Malathion
110. Mecarbam
111. Mesulfenphos
112. Metaldehyd
113. Methamidophos
114. Methiocarb
115. Methomyl
116. Methoprene
117. Metolcarb
118. Mevinphos
119. Milbemectin
120. Moxidectin
121. Naled
122. NC 184
123. NI-25, Acetamiprid
124. Nitenpyram
125. Omethoat
126. Oxamyl
127. Oxydemethon M
128. Oxydeprofos
129. Parathion
130. Parathion-methyl
131. Permethrin
132. Phenthoat
133. Phorat
134. Phosalone
135. Phosmet
136. Phoxim
137. Pirimicarb
138. Pirimiphos A
139. Pirimiphos M
140. Promecarb -continued 141. Propaphos
142. Propoxur
143. Prothiofos
144. Prothoat
145. Pyrachlophos
146. Pyradaphenthion
147. Pyresmethrin
148. Pyrethrum
149. Pyridaben
150. Pyrimidifen
151. Pyriproxyfen
152. RH 5992
153. RH-2485
154. Salithion
155. Sebufos
156. Silafluofen
157. Spinosad
158. Sulfotep
159. Sulprofos
160. Tebufenozide
161. Tebufenpyrad
162. Tebupirimphos
163. Teflubenzuron
164. Tefluthrin
165. Temephos
166. Terbam
167. Terbufos
168. Tetrachlorvinphos
169. Thiafenox
170. Thiodicarb
171. Thiofanox
172. Thionazin
173. Thuringiensin
174. Tralomethrin
175. Triarthen
176. Triazamate
177. Triazophos
178. Triazuron
179. Trichlorfon
180. Triflumuron
181. Trimethacarb
182. Vamidothion
183. XMC (3,5,-Xylyl-methyl carbamate)
184. Xylylcarb
185. YI 5301/5302
186. alpha-Cypermethrin
187. Zetamethrin Non-limitative examples of suitable anthelminthics are named in the following, a few representatives have insecticidal and acaricidal activity in addition to the anthelminthic activity, and are partly already in the above list.

(A1) Praziquantel=2-cyclohexylcarbonyl-4-oxo-1,2,3,6,7, 11b-hexahydro-4H-pyrazino[2,1-α]isoquinoline
(A2) Closantel=3,5-diiodo-N-[5-chloro-2-methyl-4-(a-cyano-4-chlorobenzyl)phenyl]-salicylamide
(A3) Triclabendazole=5-chloro-6-(2,3-dichlorophenoxy)-2-methylthio-1H-benzimidazole
(A4) Levamisol=L-(−)-2,3,5,6-tetrahydro-6-phenylimidazo [2,1b]thiazole
(A5) Mebendazole=(5-benzoyl-1H-benzimidazol-2-yl)carbaminic acid methylester
(A6) Omphalotin=a macrocyclic fermentation product of the fungus *Omphalotus olearius* described in WO 97/20857
(A7) Abamectin=avermectin B1
(A8) Ivermectin=22,23-dihydroavermectin B1
(A9) Moxidectin=5-O-demethyl-28-deoxy-25-(1,3-dimethyl-1-butenyl)-6,28-epoxy-23-(methoxyimino)-milbemycin B
(A10) Doramectin=25-cyclohexyl-5-O-demethyl-25-de(1-methylpropyl)-avermectin A1a
(A11) Milbemectin=mixture of milbemycin A3 and milbemycin A4
(A12) Milbemycinoxim=5-oxime of milbemectin The said substances are best known to specialists in this field. Most are described in various editions of the Pesticide Manual, The British Crop Protection Council, London, and others in the various editions of The Merck Index, Merck & Co., Inc., Rahway, N.J., USA or in patent literature. Therefore, the following listing is restricted to a few places where they may be found by way of example.

(I) 2-Methyl-2-(methylthio)propionaldehyde-O-methylcarbamoyloxime (Aldicarb), from The Pesticide Manual, $11^{th}$ Ed. (1997), The British Crop Protection Council, London, page 26;

(II) S-(3,4-dihydro-4-oxobenzo[d]-[1,2,3]-triazin-3-ylmethyl)O,O-dimethyl-phosphorodithioate (Azinphos-methyl), from The Pesticide Manual, $11^{th}$ Ed. (1997), The British Crop Protection Council, London, page 67;

(III) Ethyl-N-[2,3-dihydro-2,2-dimethylbenzofuran-7-yloxycarbonyl-(methyl)aminothio]-N-isopropyl-β-alaninate (Benfuracarb), from The Pesticide Manual, $11^{th}$ Ed. (1997), The British Crop Protection Council, London, page 96;

(IV) 2-Methylbiphenyl-3-ylmethyl-(Z)-(1RS)-cis-3-(2-chloro-3,3,3-trifluoroprop-1-enyl)-2,2-dimethylcyclopropanecarboxylate (Bifenthrin), from The Pesticide Manual, $11^{th}$ Ed. (1997), The British Crop Protection Council, London, page 118;

(V) 2-tert-butylimino-3-isopropyl-5-phenyl-1,3,5-thiadiazian-4-one (Buprofezin), from The Pesticide Manual, $11^{th}$ Ed. (1997), The British Crop Protection Council, London, page 157;

(VI) 2,3-Dihydro-2,2-dimethylbenzofuran-7-yl-methylcarbamate (Carbofuran), from The Pesticide Manual, $11^{th}$ Ed. (1997), The British Crop Protection Council, London, page 186;

(VII) 2,3-Dihydro-2,2-dimethylbenzofuran-7-yl-(dibutylaminothio)methylcarbamate (Carbosulfan), from The Pesticide Manual, $11^{th}$ Ed. (1997), The British Crop Protection Council, London, page 188;

(VIII) S,S'-(2-dimethylaminotrimethylene)-bis(thiocarbamate) (Cartap), from The Pesticide Manual, $11^{th}$ Ed. (1997), The British Crop Protection Council, London, page 193;

(IX) 1-[3,5-Dichloro-4-(3-chloro-5-trifluoromethyl-2-pyridyloxy)phenyl]-3-(2,6-difluorobenzoyl)-urea (Chlorfluazuron), from The Pesticide Manual, $11^{th}$ Ed. (1997), The British Crop Protection Council, London, page 213;

(X) O,O-diethyl-O-3,5,6-trichloro-2-pyridyl-phosphorothioate (Chlorpyrifos), from The Pesticide Manual, $11^{th}$ Ed. (1997), The British Crop Protection Council, London, page 235;

(XI) (RS)-α-cyano-4-fluoro-3-phenoxybenzyl-(1RS,3RS; 1RS,3RS)-3-(2,2-dichlorovinyl)-2,2-di-methylcyclopropanecarboxylate (Cyfluthrin), from The Pesticide Manual, $11^{th}$ Ed. (1997), The British Crop Protection Council, London, page 293;

(XII) Mixture of (S)-α-cyano-3-phenoxybenzyl-(Z)-(1R, 3R)-3-(2-chloro-3,3,3-trifluoropropenyl)-2,2-dimethylcyclopropanecarboxylate and (R)-α-cyano-3-phenoxybenzyl-(Z)-(1R,3R)-3-(2-chloro-3,3,3-trifluoropropenyl)-2, 2-dimethylcyclopropanecarboxylate (Lambda-Cyhalothrin), from The Pesticide Manual, $11^{th}$ Ed. (1997), The British Crop Protection Council, London, page 300;

(XIII) Racemate consisting of (S)-α-cyano-3-phenoxybenzyl-(Z)-(1R,3R)-3-(2,2-dichlorovinyl)-2,2-dimethylcyclopropanecarboxylate and (R)-α-cyano-3-phenoxybenzyl-(1S,3S)-3-(2,2-dichlorovinyl)-2,2-dimethylcyclopropanecarboxylate (Alpha-cypermethrin), from The Pesticide Manual, $11^{th}$ Ed. (1997), The British Crop Protection Council, London, page 308;

(XIV) a mixture of the stereoisomers of (S)-α-cyano-3-phenoxybenzyl (1RS,3RS,1RS,3RS)-3-(2,2-dichlorovinyl)-2,2-dimethylcyclopropanecarboxylate (zeta-Cypermethrin), from The Pesticide Manual, 11$^{th}$ Ed. (1997), The British Crop Protection Council, London, page 314;

(XV) (S)-α-cyano-3-phenoxybenzyl-(1R,3R)-3-(2,2-dibromovinyl)-2,2-dimethylcyclopropanecarboxylate (Deltamethrin), from The Pesticide Manual, 11$^{th}$ Ed. (1997), The British Crop Protection Council, London, page 344;

(XVI) (4-chlorophenyl)-3-(2,6-difluorobenzoyl)urea (Diflubenzuron), from The Pesticide Manual, 11$^{th}$ Ed. (1997), The British Crop Protection Council, London, page 395;

(XVII) (1,4,5,6,7,7-Hexachloro-8,9,10-trinorborn-5-en-2,3-ylenebismethylene)-sulphite (Endosulfan), from The Pesticide Manual, 11$^{th}$ Ed. (1997), The British Crop Protection Council, London, page 459;

(XVIII) α-ethylthio-o-tolyl-methylcarbamate (Ethiofencarb), from The Pesticide Manual, 11$^{th}$ Ed. (1997), The British Crop Protection Council, London, page 479;

(XIX) O,O-dimethyl-O-4-nitro-m-tolyl-phosphorothioate (Fenitrothion), from The Pesticide Manual, 11$^{th}$ Ed. (1997), The British Crop Protection Council, London, page 514;

(XX) 2-sec-butylphenyl-methylcarbamate (Fenobucarb), from The Pesticide Manual, 11$^{th}$ Ed. (1997), The British Crop Protection Council, London, page 516;

(XXI) (RS)-α-cyano-3-phenoxybenzyl-(RS)-2-(4-chlorophenyl)-3-methylbutyrate (Fenvalerate), from The Pesticide Manual, 11$^{th}$ Ed. (1997), The British Crop Protection Council, London, page 539;

(XXII) S-[formyl(methyl)carbamoylmethyl]-O,O-dimethyl-phosphorodithioate (Formothion), from The Pesticide Manual, 11$^{th}$ Ed. (1997), The British Crop Protection Council, London, page 625;

(XXIII) 4-Methylthio-3,5-xylyl-methylcarbamate (Methiocarb), from The Pesticide Manual, 11$^{th}$ Ed. (1997), The British Crop Protection Council, London, page 813;

(XXIV) 7-Chlorobicyclo[3.2.0]hepta-2,6-dien-6-yl-dimethylphosphate (Heptenophos), from The Pesticide Manual, 11$^{th}$ Ed. (1997), The British Crop Protection Council, London, page 670;

(XXV) 1-(6-chloro-3-pyridylmethyl)-N-nitroimidazolidin-2-ylidenamine (Imidacloprid), from The Pesticide Manual, 11$^{th}$ Ed. (1997), The British Crop Protection Council, London, page 706;

(XXVI) 2-isopropylphenyl-methylcarbamate (Isoprocarb), from The Pesticide Manual, 11$^{th}$ Ed. (1997), The British Crop Protection Council, London, page 729;

(XXVII) O,S-dimethyl-phosphoramidothioate (Methamidophos), from The Pesticide Manual, 11$^{th}$ Ed. (1997), The British Crop Protection Council, London, page 808;

(XXVIII) S-Methyl-N-(methylcarbamoyloxy)thioacetimidate (Methomyl), from The Pesticide Manual, 11$^{th}$ Ed. (1997), The British Crop Protection Council, London, page 815;

(XXIX) Methyl-3-(dimethoxyphosphinoyloxy)but-2-enoate (Mevinphos), from The Pesticide Manual, 11$^{th}$ Ed. (1997), The British Crop Protection Council, London, page 844;

(XXX) O,O-diethyl-O-4-nitrophenyl-phosphorothioate (Parathion), from The Pesticide Manual, 11$^{th}$ Ed. (1997), The British Crop Protection Council, London, page 926;

(XXXI) O,O-dimethyl-O-4-nitrophenyl-phosphorothioate (Parathion-methyl), from The Pesticide Manual, 11$^{th}$ Ed. (1997), The British Crop Protection Council, London, page 928;

(XXXII) S-6-chloro-2,3-dihydro-2-oxo-1,3-benzoxazol-3-ylmethyl-O,O-diethyl-phosphordithioate (Phosalone), from The Pesticide Manual, 11$^{th}$ Ed. (1997), The British Crop Protection Council, London, page 963;

(XXXIII) 2-Dimethylamino-5,6-dimethylpyrimidin-4-yl-dimethylcarbamate (Pirimicarb), from The Pesticide Manual, 11$^{th}$ Ed. (1997), The British Crop Protection Council, London, page 985;

(XXXIV) 2-isopropoxyphenyl-methylcarbamate (Propoxur), from The Pesticide Manual, 11$^{th}$ Ed. (1997), The British Crop Protection Council, London, page 1036;

(XXXV) 1-(3,5-dichloro-2,4-difluorophenyl)-3-(2,6-difluorobenzoyl)urea (Teflubenzuron), from The Pesticide Manual, 11$^{th}$ Ed. (1997), The British Crop Protection Council, London, page 1158;

(XXXVI) S-tert-butylthiomethyl-O,O-dimethyl-phosphorodithioate (Terbufos), from The Pesticide Manual, 11$^{th}$ Ed. (1997), The British Crop Protection Council, London, page 1165;

(XXXVII) ethyl-(3-tert.-butyl-1-dimethylcarbamoyl-1H-1,2,4-triazol-5-yl-thio)-acetate, (Triazamate), from The Pesticide Manual, 11$^{th}$ Ed. (1997), The British Crop Protection Council, London, page 1224;

(XXXVIII) Abamectin, from The Pesticide Manual, 11$^{th}$ Ed. (1997), The British Crop Protection Council, London, page 3;

(XXXIX) 2-sec-butylphenyl-methylcarbamate (Fenobucarb), from The Pesticide Manual, 11$^{th}$ Ed. (1997), The British Crop Protection Council, London, page 516;

(XL) N-tert.-butyl-N'-(4-ethylbenzoyl)-3,5-dimethylbenzohydrazide (Tebufenozide), from The Pesticide Manual, 11$^{th}$ Ed. (1997), The British Crop Protection Council, London, page 1147;

(XLI) (±)-5-amino-1-(2,6-dichloro-α,α,α-trifluoro-p-tolyl)-4-trifluoromethyl-sulphinylpyrazol-3-carbonitrile (Fipronil), from The Pesticide Manual, 11$^{th}$ Ed. (1997), The British Crop Protection Council, London, page 545;

(XLII) (RS)-α-cyano-4-fluoro-3-phenoxybenzyl(1RS,3RS;1RS,3RS)-3-(2,2-dichlorovinyl)-2,2-dimethylcyclopropanecarboxylate (beta-Cyfluthrin), from The Pesticide Manual, 11$^{th}$ Ed. (1997), The British Crop Protection Council, London, page 295;

(XLIII) (4-ethoxyphenyl)-[3-(4-fluoro-3-phenoxyphenyl)propyl](dimethyl)silane (Silafluofen), from The Pesticide Manual, 11$^{th}$ Ed. (1997), The British Crop Protection Council, London, page 1105;

(XLIV) tert.-butyl (E)-α-(1,3-dimethyl-5-phenoxypyrazol-4-yl-methylenamino-oxy)-p-toluate (Fenpyroximate), from The Pesticide Manual, 11$^{th}$ Ed. (1997), The British Crop Protection Council, London, page 530;

(XLV) 2-tert.-butyl-5-(4-tert.-butylbenzylthio)-4-chloropyridazin-3(2H)-one (Pyridaben), from The Pesticide Manual, 11$^{th}$ Ed. (1997), The British Crop Protection Council, London, page 1161;

(XLVI) 4-[[4-(1,1-dimethylphenyl)phenyl]ethoxy]-quinazoline (Fenazaquin), from The Pesticide Manual, 11$^{th}$ Ed. (1997), The British Crop Protection Council, London, page 507;

(XLVII) 4-phenoxyphenyl-(RS)-2-(pyridyloxy)propyl-ether (Pyriproxyfen), from The Pesticide Manual, 11$^{th}$ Ed. (1997), The British Crop Protection Council, London, page 1073;

(XLVIII) 5-chloro-N-{2-[4-(2-ethoxyethyl)-2,3-dimethylphenoxy]ethyl}-6-ethylpyrimidine-4-amine (Pyrimidifen), from The Pesticide Manual, 11$^{th}$ Ed. (1997), The British Crop Protection Council, London, page 1070;

(XLIX) (E)-N-(6-chloro-3-pyridylmethyl)-N-ethyl-N'-methyl-2-nitrovinylidenediamine (Nitenpyram), from The Pesticide Manual, 11$^{th}$ Ed. (1997), The British Crop Protection Council, London, page 880;
(L) (E)-N$^1$-[(6-chloro-3-pyridyl)methyl]-N$^2$-cyano-N$^1$-methylacetamidine (NI-25, Acetamiprid), from The Pesticide Manual, 11$^{th}$ Ed. (1997), The British Crop Protection Council, London, page 9;
(LI) Avermectin B$_1$, from The Pesticide Manual, 11$^{th}$ Ed. (1997), The British Crop Protection Council, London, page 3;
(LII) an insect-active extract from a plant, especially (2R,6aS,12aS)-1,2,6,6a,12,12a-hexhydro-2-isopropenyl-8,9-dimethoxy-chromeno[3,4-b]furo[2,3-h]chromen-6-one (Rotenone), from The Pesticide Manual, 11$^{th}$ Ed. (1997), The British Crop Protection Council, London, page 1097; and an extract from *Azadirachta indica*, especially azadirachtin, from The Pesticide Manual, 11$^{th}$ Ed. (1997), The British Crop Protection Council, London, page 59; and
(LIII) a preparation which contains insect-active nematodes, preferably *Heterorhabditis bacteriophora* and *Heterorhabditis megidis*, from The Pesticide Manual, 11$^{th}$ Ed. (1997), The British Crop Protection Council, London, page 671; *Steinernema feltiae*, from The Pesticide Manual, 11$^{th}$ Ed. (1997), The British Crop Protection Council, London, page 1115 and *Steinernema scapterisci*, from The Pesticide Manual, 11$^{th}$ Ed. (1997), The British Crop Protection Council, London, page 1116;
(LIV) a preparation obtainable from *Bacillus subtilis*, from The Pesticide Manual, 11$^{th}$ Ed. (1997), The British Crop Protection Council, London, page 72; or from a strain of *Bacillus thuringiensis* with the exception of compounds isolated from GC91 or from NCTC11821; The Pesticide Manual, 11$^{th}$ Ed. (1997), The British Crop Protection Council, London, page 73;
(LV) a preparation which contains insect-active fungi, preferably *Verticillium lecanii*, from The Pesticide Manual, 11$^{th}$ Ed. (1997), The British Crop Protection Council, London, page 1266; *Beauveria brogniartii*, from The Pesticide Manual, 11$^{th}$ Ed. (1997), The British Crop Protection Council, London, page 85 and *Beauveria bassiana*, from The Pesticide Manual, 11$^{th}$ Ed. (1997), The British Crop Protection Council, London, page 83;
(LVI) a preparation which contains insect-active viruses, preferably *Neodipridon Sertifer NPV*, from The Pesticide Manual, 11$^{th}$ Ed. (1997), The British Crop Protection Council, London, page 1342; *Mamestra brassicae* NPV, from The Pesticide Manual, 11$^{th}$ Ed. (1997), The British Crop Protection Council, London, page 759 and *Cydia pomonella granulosis* virus, from The Pesticide Manual, 11$^{th}$ Ed. (1997), The British Crop Protection Council, London, page 291;
(CLXXXI) 7-chloro-2,3,4a,5-tetrahydro-2-[methoxycarbonyl(4-trifluoromethoxyphenyl)-carbamoyl]indol[1,2e]oxazoline-4a-carboxylate (DPX-MP062, Indoxycarb), from The Pesticide Manual, 11$^{th}$ Ed. (1997), The British Crop Protection Council, London, page 453;
(CDXXXII) N'-tert.-butyl-N'-(3,5-dimethylbenzoyl)-3-methoxy-2-methylbenzohydrazide (RH-2485, Methoxyfenozide), from The Pesticide Manual, 11$^{th}$ Ed. (1997), The British Crop Protection Council, London, page 1094; and
(CDXXXIII) (N'[4-methoxy-biphenyl-3-yl]-hydrazinecarboxylic acid isopropylester (D 2341), from Brighton Crop Protection Conference, 1996, 487-493;
(R2) Book of Abstracts, 212th ACS National Meeting Orlando, Fla., Aug. 25-29 (1996), AGRO-020. Publisher: American Chemical Society, Washington, D.C. CONEN: 63BFAF.

A diversity of compositions are known from the field of human medicine and veterinary medicine, which are intended to ease or simplify the oral consumption of active ingredients. A few of these compositions are suitable for human application, but cannot be used for animals, and others can also be used for animals if they are problem-free active ingredients, but they have significant failings if they are unpleasant tasting or smelling active ingredients. Some are other alternatives to the present invention, but do not meet with universal acceptance by all users. The following patent specifications are mentioned by way of example:

WO 95/31963 describes an oral anthelminthic dosage form for the active ingredient flubendazole. These are lozenges based on brewer's yeast, preferably for dogs. Here, in order to increase acceptance, the active ingredient is mixed intimately with the yeast and other formulation excipients and is pressed into tablets or granulates.

WO 01/35925 describes animal feed products which contain medicaments (medicated food). The active ingredient here is not mixed directly with the feed, but is in the form of small particles, which consist of a palatable matrix, into which the active ingredient is homogeneously dispersed. In addition, these particles are provided with a protective layer.

WO 01/37808 describes solid pharmaceutical dosage forms with an improved delivery of active ingredient. It consists essentially of particles provided with an outer layer. This outer layer contains the active ingredient and at least one hydrophilic surfactant. This application form should, in particular, improve the release of hydrophobic active ingredients.

U.S. Pat. No. 4,708,867 describes an oral dosage form for the active ingredient prednisone, which consists of gelatin capsules into which small palatable particles have been filled, the capsules being coated with the active ingredient and a protective layer consisting of a copolymer of dimethylaminoethyl and methyl methacrylate.

WO 01/49272 describes palatable dosage forms for animals, based on lipid. In this application, the active ingredient is micro-encapsulated and homogeneously embedded in a melt consisting of fat, a surfactant, a filler and other excipients, and is finally processed into particles of the desired size.

WO 97/25066 describes enteric oral dosage forms for proton blockers against heartburn in human medicine. The aim of this invention is to allow the active ingredient to pass unchanged to the stomach, in order to be released in the intestines. This dosage form consists of particles of neutral carrier material, which are coated with the proton blocker and in this way have a protective coating which is resistant to hydrochloric acid. These coated particles are mixed with conventional pharmaceutical formulation excipients, and pressed into tablets or granulates which are suitable for oral administration.

In the case of the present invention, the cat has been chosen as the model of a test animal, since it is particularly choosy and fastidious regarding its eating habits. However, random testing has shown that the animal medicinal forms according to the invention, which were willingly consumed orally by cats, are also fully accepted by dogs, pigs, chickens and other domestic animals and productive livestock.

For a long time, numerous attempts have been made to find solid food material, which is so attractive to practically all cats that the cat willingly and completely eats the offered portion, even if it contains a medicinal active ingredient.

In the case of yeast tablets, e.g. of brewer's yeast, such an attractive material has been found. Yeast with its high proportion of B vitamins already has per se a positive influence on the health care of animals' skin and fur, and it is eaten very willingly by all cats.

Yeast tablets for usage by humans and animals consist of dried, pressed and lysed yeast cells. This is often so-called brewer's yeast, which occurs in large quantities in beer breweries.

If these yeast cells are mixed with an extremely bitter active ingredient, such as benazepril or another unpleasant tasting active ingredient, prior to compressing into tablets, it is observed that the test cat first of all is curious about the tablet, as would be expected, but then quickly crunches it, spits it out and turns away in disgust.

If the test is repeated, the cat already approaches the yeast tablets with mistrust and spits out the yeast even more quickly. Further repeats lead to negative conditioning, so that the cat starts to avoid yeast in general, although the yeast was originally very attractive.

It is also of no use to coat the yeast tablet with a layer of neutral taste, since the yeast then loses its natural attraction and acceptance and is rejected by the cat from the start. It is then not even prepared to try out the placebo.

By simply mixing the active ingredient, clearly the problem has not been solved.

If the bitter active ingredient is firstly micro-encapsulated or embedded in particles consisting of a neutral matrix, e.g. modified starch, acceptance by individual cats is increased in the short term, but the long-term test likewise results in negative conditioning.

It has now surprisingly been found that, by combining a series of basically four relatively simple technical measures, the taste or acceptance problem of orally administering medicaments to animals can in fact be solved to full satisfaction. This application form thereby becomes safe and user-friendly.

The following measures are involved:

One starts with a neutral-tasting, physiologically compatible, solid, fine-grained carrier material, preferably small balls, granulates, grains, etc. For the sake of simplicity, this fine-grained carrier material is referred to hereinafter as particles.

Said particles are coated with the active ingredient, so that the active ingredient encases the particles.

This active ingredient casing is coated with a masking protective layer consisting of a physiologically compatible polymer matrix, which prevents direct contact of the active ingredient with the gustatory cells in the animal's mouth.

These particles prepared in this manner are intimately mixed with a substrate which is attractive to animals and pressed into tablets or pellets of a suitable size.

A deciding factor to animal acceptance is, however, the size of the coated particles. It has been shown that particles with a diameter above 0.8 mm do not lead to reproducible acceptance. In contrast, reliable results are achieved with diameters of less than 0.4 mm even with very choosy cats. A lower limit for the diameter is not indicated per se, since at best full acceptance can be achieved also with such small diameters. For manufacturing and cost reasons, the lower limit is ca. 0.09 mm.

The process for the production of such a palatable and thus attractive animal medicine is therefore characterised in particular in that:

(a) neutral-tasting, physiologically compatible, solid, fine-grained particles with an average diameter of 0.09 to 0.8 mm, preferably 0.15 to 0.4 mm, are encased by the active ingredient;

(b) this active ingredient casing is coated with a masking protective layer consisting of a physiologically compatible polymer matrix;

(c) these double-coated particles, namely firstly coated with the active ingredient and then with the polymer matrix, and therefore masked particles, are introduced into a physiologically compatible substrate which is attractive to animals; and (d) the substrate-particle mixture is pressed into tablets or pellets.

Suitable physiologically compatible carrier materials for producing the particles may be numerous solid formulation excipients, which are known from the production of pharmaceutical medicaments, e.g. cellulose, starch, saccharose, lactose or other different types of sugar.

In order to encase the particles, the generally solid active ingredient is conveniently dissolved in a suitable, physiologically acceptable solvent or solvent mixture, e.g. a low-boiling alcohol, or alcohol-water mixture, for example ethanol:water (1:1), and applied to the particles by a spraying process. Very many solvents are suitable. The readily volatile solvents are preferably selected. After the spraying procedure, the solvent or solvent mixture is removed, at best under careful conditions, e.g. in a vacuum.

These particles coated with active ingredient are not yet suitable for oral administration in this form and are now coated with a protective layer consisting of a physiologically compatible polymer matrix and are thus masked.

By 'masked' in connection with the present invention is understood screening of the active ingredient against the action of saliva and its constituents upon oral administration, and the protection of the active ingredient thereby obtained against contact with the gustatory and olfactory cells in the mouth, throat and nose of the animal. A masked active ingredient has neutral behaviour, i.e. a neutral taste and smell.

Polymers which are suitable for masking have been known for a long time in the production of medicaments. Suitable classes of polymer are e.g. those selected from the group consisting of: shellac, a polymer on a cellulose, acrylic acid or methacrylic acid, maleic acid anhydride, polyvinyl pyrrolidone and polyvinyl alcohol basis. The shellac in question is often used to coat coated tablets. However, other polymers may also be considered, e.g. polymers on a cellulose basis, which are produced for example from cellulose acetate phthalate or cellulose acetate-N,N-di-n-butylhydroxypropylether. The starting materials for polymers on an acrylic acid or methacrylic acid basis may be e.g. methacrylate/methacrylic acid copolymer, 2-methyl-5-vinyl-pyridine/methacrylate/methacrylic acid copolymer, methyl methacrylate/methacrylic acid copolymer, methyl methacrylate/methacrylic acid copolymer, methyl methacrylate/maleic acid anhydride copolymer or methyl methacrylate/maleic acid anhydride copolymer.

Suitable starting materials for polymers on a maleic acid anhydride basis are e.g. vinyl-methylether/maleic acid anhydride copolymer or styrene/maleic acid anhydride copolymer. Polymers on an acrylic acid or methacrylic acid basis are most preferred as a casing for the microspheres in the context of the present invention. It is best to use commercial products for their production. These are polymerisation products of acrylic acid and acrylic acid esters with a low content of quaternary ammonium groups. Owing to their easy handling, commercial products, such as Eudragit® E, L or S from the company Röhm, Darmstadt, Germany, are especially suitable. Eudragit® E is a cationic polymer of dimethylaminoethyl methacrylate and a neutral methacrylic acid ester.

Eudragit® L and S are anionic copolymers of methacrylic acid and methacrylic acid methylester.

Polyvinyl pyrrolidone is suitable e.g. as a starting material for polymers on a polyvinyl pyrrolidone basis. Polyvinyl alcohol itself is suitable as a starting material for polymers on a polyvinyl alcohol basis. Eudragit® E 100 is a pH-dependent cationic polymer, which dissolves in the gastric juices at an acidic pH value of up to pH 5.0. Above pH 5.0, it is capable of swelling and eminently suitable for coating and masking. In powder form, it is known commercially as Eudragit® EPO. Eudragit® EPO has the advantage that the process can be carried out in an aqueous medium and without organic solvents.

Masking is effected in such a way that the shellac or the polymer is dissolved in an organic solvent optionally adding water, and this solution is sprayed by a spraying process onto the particles which are already encased by the active ingredient. The solvent or solvent mixture is subsequently removed under careful conditions, e.g. in a vacuum.

Suitable organic solvents for dissolution of the polymer are, for example, solvents which are relatively readily volatile. The following table shows a few such solvents by way of example.

TABLE 1

| solvent | dielectricity constant | x | solvent | dielectricity constant |
|---|---|---|---|---|
| methanol | 32.6 | | phenol | 9.8 |
| ethanol | 24.3 | | acetone | 20.7 |
| isopropanol | 18.7 | | acetic acid | 9.7 |
| butanol | 17.1 | | acetic acid anhydride | 20.7 |
| benzyl alcohol | 13.1 | | nitromethane | 35.9 |
| ethylene glycol | 37.7 | | ethylene diamine | 14.2 |
| propylene glycol | 35.0 | | acetic acid cellosolve | 16 |

The pure solvents or mixtures of such solvents may be used, e.g. an acetone-ethanol mixture (1:1). Very good results are obtained by adding a little water, i.e. about 1 to 5 parts by volume of water to 10 to 50 parts by volume of organic solvent. Acetone-water mixtures (ca. 1:30) are preferred.

Furthermore, aqueous suspensions and solutions may be used. In the example described below, coating is carried out with EUDRAGIT EPO from an aqueous suspension. This has the advantage that in the commercial preparation of a product, no measures to protect against explosion need be taken. In addition, an aqueous process is to be recommended for environmental protection reasons, since no organic solvents reach the environment or have to be extracted in an expensive procedure.

In a final operation, the masked particles are mixed with a feed material of high acceptance, e.g. the yeasts mentioned above, and are pressed into suitable administrable units, such as tablets or feed pellets. By adding artificial or natural aromas, the attractivity of the yeast and other suitable substrates can be substantially increased.

The procedure is carried out in detail as follows: The active ingredient is applied advantageously in a fluidised bed process to the neutral-tasting, physiologically compatible, solid, fine-grained particles and subsequently masked. To do so, a layer of said particles is added to a reaction container having a sieve-like base. A gas, preferably air, is passed through this layer against the force of gravity. The flow speed is chosen such that the layer is whirled up until the individual particles no longer touch and can be held in the suspension, so that a stationary fluidised bed is obtained. In this way, the whole surface of each individual particle is accessible. A precisely measured solution, emulsion or suspension of the active ingredient is sprayed, in the opposite direction to a stream of gas, through a spray nozzle which is usually approximately in the centre of the stationary fluidised bed. In the example which follows, this was carried out by the so-called Wurster process (bottom spray process), since the best results in respect of yield and process time were achieved in this way. However, in principle, any type of fluidised bed process is suitable. Through the whirling action, the particles are moistened with the solution, emulsion or suspension of active ingredient. Subsequently, the supply of active ingredient is stopped and the particles continue to whirl and are dried by the streaming gas. Warmed gas may be used to accelerate the drying procedure. The degree of warming depends on the heat stability of the active ingredient used. The outcome of the drying procedure is that the active ingredient crystallises on the surface of the particles. In a further operation, a solution of the physiologically compatible polymer matrix is sprayed through the spray nozzle, with the result that the particles receive a second coating which thus masks the active ingredient. Drying of the masking layer takes place in the same way as for the active ingredient, in the stream of gas. The end product obtained is the desired, double-coated, free-flowing particles, which do not have a tendency to agglomerate and are mixed according to the invention with an appropriate substrate and in a final step are pressed into tablets or pellets.

The double coating guarantees excellent palatability, meaning the all the senses perceived by the sensory cells for taste and smell in the mouth and nose areas.

The size of the coated particles have been shown to be essential to the invention and crucial to acceptance of the finished product. As already mentioned, surprisingly, they may not exceed a certain minimum size. If relatively small, compact carrier particles of 0.09 to 0.8 mm, preferably 0.15 to 0.4 mm diameter are produced, coated with the active ingredient, then encased with a layer which masks the taste and if these encased particles are then mixed with yeast or another suitable feed material, and the mixture is pressed into tablets or feed pellets, it is observed that these yeast tablets or feed pellets are eaten just as willingly by cats as tablets or pellets without active ingredient, i.e. placebos. Clearly, the cat no longer sniffs out the active ingredient. As has now been discovered, the coated particles must however be of exactly the correct size and have the said double coating, so that only very few of them, or practically none at all, are destroyed when the yeast tablet is crunched and practically no active ingredient is released. As the size of the coated particles increases, the acceptance by cats decreases. Particles with a diameter of 0.15 to 0.4 mm have proved to be ideal. The larger the particles, the more likely it is that some of them will be bitten and more bitter active ingredient will be released. The particles themselves cannot be made too small, as the lower limit is determined by the available manufacturing technology and by the technical efforts that one is prepared to make. These double-coated particles are also significantly better accepted than particles of the same size, in which the active ingredient is homogeneously incorporated, and also significantly better than particles of the same size, which are encased with the active ingredient, but in which a further protective layer is missing.

By attractive, physiologically compatible substrate in connection with the present invention is understood for example the yeast mentioned initially, but also organic material of vegetable or animal origin, which is usually used as a dry feed for the species of animal to be treated, and is either already attractive to the animal to be treated because of its origin, or is made attractive by adding artificial or natural aromatic substances or taste improvers. Suitable aromatic substances or taste improvers are natural or synthetic meat, fish and cheese aromas. Natural or artificial vanilla essence is also eminently suitable. A whole range of such substances is available to the nutrition specialist. These substances are commercial and are used on a large scale in the animal feed industry.

It has now been shown that active substances used in the production of feed pellets and tablets behave in an extremely stable manner if they are used in the form of the masked particles according to the invention. In most cases, a measurable loss of active ingredient is not observed over a period of months.

The preferred embodiments of the present invention include:

A animal medicine consisting of a substrate in pellet or tablet form, which is attractive to livestock and domestic animals, in which fine-grained particles of a neutral-tasting, physiologically compatible, solid carrier material are embedded, which is characterised in that said fine-grained particles of carrier material have an average diameter of 0.09 to 0.8 mm and are coated with an active substance for veterinary medicine, and said active substance layer is encased with a protective layer of a physiologically compatible polymer matrix.

The said animal medicine, in which the fine-grained particles of carrier material have an average diameter of 0.15 to 0.4 mm.

The said animal medicine, in which the fine-grained particles of carrier material consist of cellulose, starch, saccharose, lactose or sugar.

The said animal medicine, in which the said physiologically compatible polymer matrix is selected from the group consisting of: shellac, a polymer on a cellulose, acrylic acid or methacrylic acid, maleic acid anhydride, polyvinyl pyrrolidone and polyvinyl alcohol basis.

The said animal medicine, in which the substrate which is attractive to livestock and domestic animals is a dry feed for animals on a vegetable and/or animal basis, which optionally contains additives, such as proteins, vitamins, minerals or artificial or natural aromatics.

The said animal medicine, in which the substrate which is attractive to livestock and domestic animals is lysed yeast.

The said animal medicine, which contains natural and artificial cheese, meat and fish aromas or flavour enhancers which are known from the foodstuffs industry or vanilla essence.

The said animal medicines, which contain as the active substance for veterinary medicine an active ingredient or mixture of active ingredients, which are used against external or internal parasites, viral or bacterial diseases, behavioural disorders or dysfunction or hypo-activity.

The said animal medicine, which contains as the active substance for veterinary medicine an active substance which has an unpleasant taste for the animal, preferably benazepril.

A process for the production of one of the said animal medicines, which is characterised in that (1) particles with an average diameter of 0.09 to 0.8 mm of a neutral-tasting, physiologically compatible, solid carrier material are coated with an active ingredient or active ingredient for veterinary medicine, so that the active ingredient encases the particles;

(2) this active ingredient casing is coated with a masking protective layer consisting of a physiologically compatible polymer matrix, which prevents direct contact of the active ingredient with the gustatory and olfactory cells and the saliva of the animal.

(3) these double-coated particles are intimately mixed with a substrate which is attractive to the animal; and (4) the mixture consisting of substrate and double-coated particles is compressed into administrable units of an appropriate size.

the said process, which is characterised in that the particles in stage (1) have an average diameter of 0.15 to 0.4 mm.

the said process, which is characterised in that the particles in stage (1) consist of cellulose, starch, saccharose, lactose or sugar.

the said process, which is characterised in that the polymer matrix in stage (2) is selected from the group consisting of: shellac, a polymer on a cellulose, acrylic acid or methacrylic acid, maleic acid anhydride, polyvinyl pyrrolidone and polyvinyl alcohol basis.

the said process, which is characterised in that the substrate in stage (3) which is attractive to the animal is a dry feed material for animals on a vegetable and/or animal basis, which contains optional additives, such as proteins, vitamins, minerals or artificial or natural aromatic substances.

the said process, which is characterised in that the substrate in stage (3) which is attractive to the animal is lysed yeast.

the said process, which is characterised in that the substrate in stage (3) which is attractive to the animal contains natural and artificial cheese, meat and fish aromas or flavour enhancers which are known from the foodstuffs industry or vanilla essence.

the said process, which is characterised in that the active ingredient or active ingredient mixture for veterinary medicine in stage (1) is an active ingredient or mixture of active ingredients, which are used against external or internal parasites, viral or bacterial diseases, behavioural disorders or dysfunction or hypo-activity.

the said process, which is characterised in that, in order to coat the particles in stage (1), the solid active ingredient or active ingredient mixture is dissolved in a suitable physiologically acceptable solvent or solvent mixture, applied to the particles by a spraying process and, after the spraying procedure, the solvent or solvent mixture is carefully removed.

the said process, which is characterised in that, in order to apply the polymer matrix in stage (2), the shellac or the polymer is dissolved or dispersed in an organic solvent optionally adding water, and this solution or dispersion is sprayed by a spraying process onto the particles which are already encased by the active ingredient. The solvent or solvent mixture is subsequently removed under careful conditions.

the usage of the double-coated particles produced in stage (2) for producing a veterinary medicine preparation.

PREPARATION EXAMPLES

1. Preparation of a Solution of Benazepril

| Composition | Weight |
| --- | --- |
| benazepril HCl (active substance) | 2.856 kg |
| Excipients | |
| ethanol 96% | 8.16 kg |
| water | 12.24 kg |
| polyvinyl polypyrrolidone | 1.071 kg |

Ethanol and water are mixed in a vessel until a homogeneous solution is formed. Benazepril hydrochloride is added to the solvent mixture and stirred for 5 minutes until a clear solution is obtained. Polyvinyl polypyrrolidone is subsequently added and stirred for a further 10 minutes until a clear solution is obtained.

2. Coating of Particles with Benazepril

| Excipients | Weight |
| --- | --- |
| Celphere CP 203 ®* | 31.15 kg |

Celphere ® is a commercial product of the company ASAHI, Japan. It consists of round microcrystalline cellulose particles or pellets.

Typical Celphere pellets have the following properties:

| | product name | | | |
| --- | --- | --- | --- | --- |
| property | CP-102 | CP-203 | CP-305 | CP-507 |
| particle size μm) | 106-212 | 150-300 | 300-500 | 500-710 |
| spherical deviation* | 1.2 | 1.1 | 1.1 | 1.2 |
| density (g/cm$^3$) | 0.87 | 0.87 | 0.97 | 0.97 |
| loss on drying (%) | 4 | 4 | 4 | 4 |
| friability in air (%) | 0 | 0 | 0 | 0 |
| in water (%) | 0 | 0 | 0 | 2 |
| in ethanol (%) | 0 | 0 | 0 | 0 |
| water absorption (%) | 100 | 100 | 100 | 70 |
| colour and odour | white to yellowish odourless | | | |
| solubility | insoluble in water, ethanol & other organic solvents | | | |

*spherical deviation = ratio of the longer to the shorter axis

Celphere pellets are placed in fluidised bed equipment and heated to a product temperature of 35° C. The required amount of active ingredient solution, here: benazepril solution, see point 1 (23.9 kg) is sprayed onto the pellets. After spraying, the pellets are dried at an admission temperature of 55° C. until attaining residual moisture of <4%. The pellets are subsequently sieved through a 0.5 mm sieve. The yield of benazepril pellets is >95%. Outstanding pellets are obtained by coating CP-102, CP-203 and CP-305 or substrate particles, which have the same average diameter.

3. Masking of the Particles

| Excipients | Weight |
| --- | --- |
| sodium lauryl sulphate | 0.75 kg |
| dibutyl sebacate | 1.61 kg |
| Eudragit EPO ®* | 10.71 kg |
| Syloid 244 FP ® | 4.28 kg |
| water | 89.75 kg |
| Aerosil 200 ® | 0.26 kg |

Eudragit ® is a commercial product of the company Röhm, Germany. It consists of butyl methacrylate-(2-dimethylaminoethyl)methacrylate-methylmethacrylate copolymer (1:2:1).
Syloid 244 FP ® is a precipitated silicon dioxide, which is obtainable from the company Grace GmbH, in Worms, Germany. Aerosil 200 ® is colloidal silicon dioxide from the company Degussa in Frankfurt/Main, Germany.

Sodium lauryl sulphate and dibutyl sebacate are dissolved in 89.75 kg of water. Subsequently, the Eudragit EPO® is added to the solution and carefully stirred for at least 3 hours until a homogeneous suspension is obtained. Syloid 244 FP® is added and the mixture is stirred until a homogeneous suspension is produced. In order to remove larger particles from the suspension, the solution is sieved through a 1.0 mm sieve before coating the active ingredient pellet. During the entire coating process, the spray suspension is carefully stirred, so that no particles can settle in the vessel. Then, 35 kg of active ingredient pellets are filled into the fluidised bed equipment and heated to a product temperature of 28° C. The coating suspension is sprayed onto the active ingredient pellets. After spraying, the pellets are dried at an admission temperature of 55° C. until attaining residual moisture of <4%. The pellets are subsequently sifted through a 0.5 mm sieve. The yield of benazepril pellets is >90%. In order to avoid adhesion of the taste-masked pellets during storage, 0.26 kg of Aerosil 200® are sifted onto the pellets through a 1.4 mm sieve. The dry mixture is mixed for 10 minutes in a drum mixer.

4. Preparation of Yeast Tablets with 22.5 kg of Taste-Masked Benazepril Pellets

| Excipients | Weight |
| --- | --- |
| Avicel PH 102 ® | 9.0 kg |
| yeast powder (lysed brewer's yeast) | 49.5 kg |
| polyvinyl polypyrrolidone | 4.5 kg |
| Aerosil 200 ® | 0.45 kg |
| vanilla | 0.45 kg |
| hydrogenated castor oil | 3.6 kg |

Avicel PH 102 ® is a microcrystalline cellulose of the company FMC Corporation in Philadelphia, USA.

The benazepril pellets already prepared (5% active ingredient), as well as Avicel PH 102®, yeast powder, polyvinyl polypyrrolidone, Aerosil® and vanilla are sifted through a 0.75 mm sieve into a drum and mixed for 30 minutes at a speed of 15 rpm. Subsequently, the hydrogenated castor oil is added to the mixture, the whole mixture is sifted through a 0.75 mm sieve and mixed for 15 minutes. This powder mixture is then pressed into tablets.

5. Feeding Test on Cats (Acceptance Test)

10 adult cats are used to test the acceptance of various tablets based on yeast. The procedure takes place as follows:

1. The tablets are offered from the hand. If the cat does not take the tablet within 1 minute, 2. the tablet is placed in the empty feeding bowl. The cat is again allowed 1 minute to eat the tablet. If this does not take place again, it is placed in the cat's mouth and left for another 1 minute. If none of these tests leads to acceptance of the tablet, this is evaluated as non-acceptance. If one of the three above-mentioned offers leads to the cat willingly eating the tablet, this is evaluated as acceptance of the tablet. These tests are repeated over three days.

The maximum palatability of cats is reached with a yeast proportion in the tablet of 50%. For the pure yeast tablets (placebo), this lies at 68% acceptance and for yeast tablets combined with fish aroma it is 60%. By increasing the proportion of yeast and adding vanilla aromas, palatability can be increased to 90%. The combination of yeast with vanilla shows the greatest palatability.

What we claim is:

1. A composition for consumption by a dog comprising:
   an animal feed substrate which is yeast; and
   one or more coated particles, wherein said substrate and said coated particles are intimately mixed and pressed into tablets or pellets of suitable size for feed consumption by a dog, said intimate mixture of substrate and coated particles optionally comprising one or more additives selected from the group consisting of proteins, vitamins, minerals, artificial aromatics, and natural aromatics and wherein said coated particles consist of:
      a carrier material having an average diameter of approximately 0.09 mm to 0.8 mm, wherein said carrier material is cellulose;
      a first coat which is a casing consisting of benazepril and polyvinyl pyrrolidone; and
      a second coat comprising a physiologically compatible cationic polymer matrix, wherein said physiologically compatible cationic polymer matrix is an acrylic acid polymer or a methacrylic acid polymer or a combination of said polymers.

2. The composition of claim 1 wherein the carrier material has an average diameter of approximately 0.15 mm to 0.4 mm.

3. The composition of claim 1 wherein the cationic polymer is based on diaminoethyl methacrylate and neutral methacrylic esters.

4. A method of making the composition of claim 1, said method comprising:
   mixing benazepril with a solvent;
   coating a carrier material with the benazepril dissolved in a solvent, wherein said carrier material has an average diameter of approximately 0.09 mm to 0.8 mm, and wherein said carrier material is cellulose;
   coating said benazepril-coated carrier material with an additional cationic masking protective layer to form multi-coated particles, wherein said cationic masking protective layer is an acrylic add polymer or a methacrylic acid polymer or a combination of said polymers;
   intimately mixing said multi-coated particles with a substrate wherein said substrate consists of yeast; and
   compressing said intimately mixed coated particles and substrate into tablets or pellets of appropriate size for feed consumption.

5. The method of claim 4 further comprising adding one or more additives to said intimately mixed coated particles and substrate wherein said additive is selected from the group consisting of proteins, vitamins, minerals, artificial aromatic substances, and natural aromatic substances.

6. The method of claim 4 wherein the carrier material has an average diameter of approximately 0.15 mm to 0.4 mm.

7. The method of claim 4 wherein the cationic polymer is based on dimethylaminoethyl methacrylate and neutral methacrylic esters.

* * * * *